US009125846B2

(12) United States Patent
Kayed

(10) Patent No.: US 9,125,846 B2
(45) Date of Patent: Sep. 8, 2015

(54) ANTIBODIES THAT BIND AMYLOID OLIGOMERS

(75) Inventor: Rakez Kayed, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 280 days.

(21) Appl. No.: 13/273,507

(22) Filed: Oct. 14, 2011

(65) Prior Publication Data

US 2012/0148591 A1 Jun. 14, 2012

Related U.S. Application Data

(60) Provisional application No. 61/393,685, filed on Oct. 15, 2010.

(51) Int. Cl.
*A61K 39/395* (2006.01)
*A61K 39/00* (2006.01)
*G01N 33/68* (2006.01)
*C07K 16/18* (2006.01)

(52) U.S. Cl.
CPC .............. *A61K 39/0007* (2013.01); *C07K 16/18* (2013.01); *G01N 33/6896* (2013.01); *A61K 2039/55566* (2013.01); *G01N 2800/042* (2013.01); *G01N 2800/2821* (2013.01); *G01N 2800/2828* (2013.01); *G01N 2800/2835* (2013.01)

(58) Field of Classification Search
CPC .............. C07K 16/18; G01N 33/6896; G01N 2800/2821; G01N 2800/2828; G01N 2800/2835; G01N 2800/042; A61K 39/0007; A61K 2039/55566
See application file for complete search history.

(56) References Cited

U.S. PATENT DOCUMENTS

| | | | |
|---|---|---|---|
| 5,693,762 A * | 12/1997 | Queen et al. ............... | 530/387.3 |
| 7,439,041 B2 | 10/2008 | Michelitsch | |
| 2004/0005643 A1 | 1/2004 | De Santis et al. | |
| 2004/0137421 A1 | 7/2004 | Kitamoto et al. | |
| 2007/0218491 A1 | 9/2007 | Vasan et al. | |
| 2008/0050383 A1 | 2/2008 | Sigurdsson et al. | |
| 2008/0220449 A1 | 9/2008 | Vasan et al. | |
| 2009/0075984 A1 | 3/2009 | Wischik et al. | |
| 2009/0123936 A1 | 5/2009 | Novak | |
| 2009/0162336 A1 | 6/2009 | Mandelkow et al. | |
| 2009/0258009 A1 | 10/2009 | Gellefors et al. | |
| 2010/0209422 A1 | 8/2010 | Revetch et al. | |

FOREIGN PATENT DOCUMENTS

WO    WO 2005061544 A2 *   7/2005
WO    WO2005061545         7/2005

OTHER PUBLICATIONS

Guerrero et al. Characterization and relevance of novel anti-oligomer mouse monoclonal antibody. Society for Neuroscience Abstract Viewer and Itinerary Planner, vol. 40, 2010, first publicly available Aug. 15, 2010.*
Sengupta et al. Tau oligomers in Parkinson disease and dementia with Lewy bodies and their connection with alpha-synuclein oligomers. Society for Neuroscience Abstract Viewer and Itinerary Planner, vol. 40, 2010, first publicly available Aug. 15, 2010.*
Cardinale et al., The potential of intracellular antibodies for therapeutic targeting of protein-misfolding diseases. Trends Mol Med. Sep. 2008 (Epub Aug. 5, 2008), vol. 14, No. 9, pp. 373-380.
Maguire-Zeiss et al., Identification of human alpha-synuclein specific single chain antibodies. Biochem Biophys Res Commun., Nov. 3, 2006, vol. 349, No. 4, pp. 1198-1205.
Lindblad, Aluminium compounds for use in vaccines. Immunol Cell Biol., Oct. 2004, vol. 82, No. 5, pp. 497-505.
Kayed et al., Conformation-dependent anti-amyloid oligomer antibodies. Methods Enzymol. 2006, vol. 413, pp. 326-344.
Asuni et al. Immunotherapy targeting pathological tau conformers in a tangle mouse model reduces brain pathology with associated functional improvements. J Neurosci. Aug. 22, 2007, vol. 27, No. 34, pp. 9115-9129.
Barrantes et al., Tau Aggregation Followed by Atomic Force Microscopy and Surface Plasmon Resonance, and Single Molecule Tau-Tau Interaction Probed by Atomic Force Spectroscopy. Journal of Alzheimer's Disease, 2009 (EPub Jul. 20, 2009), vol. 18, No. 1, pp. 141-151.
Sahara et al., Tau oligomerization: a role for tau aggregation intermediates linked to neurodegeneration. Curr Alzheimer Res., Dec. 2008, vol. 5, No. 6, pp. 591-598.
Maeda et al., Granular tau oligomers as intermediates of tau filaments. Biochemistry, Mar. 27, 2007, vol. 46, No. 12, pp. 3856-3861.
Hamano. Concentration-dependent Effects of Proteasomal Inhibition on tau Processing in a Cellular Mode. Int J Clin Exp Pathol. ePub Jun. 15, 2009; 2(6): 561-573.
International Preliminary Report on Patentability, PCT/US2010/047154.
Goedert et al., EMBO J., 8:393-399, 1989.
Goedert et al., Neuron., 3:519-526, 1989.
Jakes et al., EMBO J., 10:2725-2729, 1991.
Wischik et al., Proc. Natl. Acad. Sci. USA, 93:11213-11218, 1996.
Mena et al., Acta Neuropathol., 89:50-56, 1995.
Mena et al., Acta Neuropathol., 91:633-641, 1996.
Lai et al., Neurobiology of Ageing, 16(3):433-445, 1995.
Wischik et al., Proc. Natl. Acad. Sci. USA, 85:4884-4888, 1998a.
Spires-Jones et al., Trends Neurosci., 32(3):150-9, 2009.
Augustinack et al., Acta Neuropathol., 103(1):26-35, 2002.
Busciglio et al., Neuron., 14(4):879-88, 1995.
Avila et al., Curr. Alzheimer Res., 1(2):97-101, 2004.
Honson et al., Neurotox. Res., 15(3):274-83, 2009.
Iqbal et al., Acta Neuropathol., 118(1):53-69, 2009.
Hardy and Selkoe, Science, 7(5580):353-6, 2002.
Alafuzoff et al., Brain Pathol., 18(4):484-96, 2008.
Braak and Braak, Acta Neurol. Scand. Suppl., 165:3-12, 1996.
Santacruz et al., Science, 309(5733):476-81, 2005.
Oddo et al., J. Biol. Chem., 281(51):39413-23, 2006.

(Continued)

*Primary Examiner* — Gregory S Emch
(74) *Attorney, Agent, or Firm* — Norton Rose Fulbright US LLP

(57) ABSTRACT

Embodiments of the invention are directed to compositions and methods related to immunogenic compositions comprising the amino acid sequence of SEQ ID NO:1 and amyloid oligomer specific antibodies that specifically bind an oligomer comprising such a peptide.

7 Claims, 9 Drawing Sheets

(56) References Cited

OTHER PUBLICATIONS

Congdon and Duff, J. Alzheimers Dis., 14(4):453-7, 2008.
Brunden et al., J. Alzheimers Dis., 14(4):393-9, 2008.
Kurt et al., Neurobiol. Dis., 14(1):89-97, 2003.
Kayed and Glabe, The SFN 36th annual meeting 2006, poster# 17.6.
De Felice et al., Neurobiol. Aging, 29(9):1334-47, 2008.
Vieira et al., J. Neurochem., 103(2):736-48, 2007.
Margittai and Langen, Proc. Natl. Acad. Sci. USA, 101(28):10278-83, 2004.
Margittai and Langen, J. Biol. Chem., 281(49):37820-7, 2006.
Kayed and Glabe, Methods Enzymol., 413:326-44, 2006.
Kayed et al., J. Biol. Chem., 279(45):46363-6, 2004.
Kayed et al., Science, 300(5618):486-9., 2003.
Borroni et al., Eur. J. Pharmacol., 545(1):73-80, 2006.
Wiltfang et al., World J. Biol. Psychiatry, 6(2):69-84, 2005.
Andreasen et al., Neurosci. Lett., 273(1):5-8, 1999.
Galasko et al., Neurology, 48(3):632-5, 1997.
Vandermeeren et al., J. Neurochem., 61(5):1828-34, 1993.
Zetterberg et al., Neurosci. Lett., 352(1):67-9, 2003.
Herukka et al., Neurology, 64(7):1294-7, 2005.
Buerger et al., Brain, 129(Pt 11):3035-41, 2006.
Parnetti et al., Mech. Ageing Dev., 127(2):129-32, 2006.
Shaw et al., Ann. Neurol., 65(4):403-13, 2009.
Li et al., Neurology, 69(7):631-9, 2007.
Blom et al., Dement. Geriatr. Cogn. Disord., 27(5):458-64, 2009.
Ringman et al., Neurology, 71(2):85-92, 2008.
Ballatore et al., Nat. Rev. Neurosci., 8(9):663-72, 2007.
Haroutunian et al., Neurobiol. Aging, 28(1):1-7, 2007.
Schneider and Mandelkow, Neurotherapeutics, 5(3):443-57, 2008.
Bretteville and Planel, J. Alzheimers Dis., 14(4):431-6, 2008.
Hernandez and Avila, J. Alzheimers Dis., 14(4):449-52, 2008.
Marx, Science, 316(5830):1416-7, 2007.
Walsh and Selkoe, J. Neurochem., 101(5):1172-84, 2007.
Gomez-Ramos et al., Mol. Cell Neurosci., 37(4):673-81, 2008.
Berger et al., J. Neurosci., 27(14):3650-62, 2007.
Kayed et al., WO 2004/024090, Mar. 25, 2004.
Jones et al., 2000, Development Dynamics 218:235-259.
Rosenmann et al., 2006, Arch. Neurol. 63: 1459-1467.
Deture et al., 2004, Am. J. Pathol 161(5): 1711-1722.
Gamblin et al., 2003, Proc. Nat. Acad. Sci. 100(17): 10032-10037.
Honson and Kuret, 2008, J. Alzheimer's Dis. 14(4): 417-422.
Kayed and Jackson, 2009, Curr Opin Immunol 21:359-363.
Sahara et al. 2002, J. Neurochem. 83: 1498-1508.
Yoshiyama et al., 2007, Neuron 53: 337-351.
EP Search Report 10812710.1, Mar. 3, 2013.
Asuni et al., 2007, Journal of Neuroscience 27(34):9115-9129.
Rosenmann et al., 2006, Arch Neurol 63:-1459-1467.
Barrantes et al. 2009, Journal of Alzheimer's Disease 18:141-151.
UTMB0294WO International Search Report PCT/US2011/056293.
Kayed and Glabe, Oct. 14,2006, Oasis Online Abstract Submission and Invitation System.
Haines et al. Germline diversity of the expressed BALB/c VhJ558 gene family. Mol. Immunol. 38(1), 9-18 (2001).

* cited by examiner

- Oligo A: Coated with 50ng of Aβ oligo mimics.
- Oligo B: Coated with 50ng of prion oligo mimics.

ANTIBODIES THAT BIND AMYLOID OLIGOMERS

This application claims priority to U.S. Provisional Application No. 61/393,685 filed Oct. 15, 2010, which is incorporated in its entirety herein by reference.

REFERENCE TO SEQUENCE LISTING

A sequence listing required by 37 CFR 1.821-1.825 is being submitted electronically with this application. The sequence listing is incorporated herein by reference.

BACKGROUND OF THE INVENTION

I. Field of the Invention

Embodiments of this invention are directed generally to biology and medicine. In certain aspects, embodiments are directed to compositions and methods related to amyloid oligomers and amyloid oligomer specific antibodies, particularly mouse monoclonal antibodies.

II. Background

Many biological functions come about, at least in part, due to the ability of proteins to adopt various sequence-dependent structures. However, certain protein sequences can sometimes form aberrant, misfolded, insoluble aggregates known as amyloid fibrils. These amyloid fibrils are thought to be involved in the pathogenesis of various amyloid diseases of genetic, infectious and/or spontaneous origin, including spongiform encephalopathies, Alzheimer's disease (AD), Parkinson's disease (PD), type II diabetes, Creutzfeldt-Jakob disease, Huntington's disease, possibly macular degeneration, various prion diseases and numerous others. In at least some of these amyloid diseases, amyloid fibrils lead to the development of amyloid plaques.

Amyloid peptides are the principal constituent of amyloid plaques. In the case of Alzheimer's disease, the peptides are termed Aβ or β-amyloid peptide. Aβ peptide is an internal fragment of 39 to 43 amino acids of amyloid precursor protein (APP). Several mutations within the APP protein have been correlated with the presence of AD. See, for example, Goate et al., Nature, (1991) 349:704 (valine to isoleucine); Chartier Marian et al., Nature (1991) 353:844 (valine to glycine); Murrell et al. Science (1991) 21:97 (valine to phenylalanine); Mullan et al., Nature Genet. (1992) 1:345 (a double mutation changing lysine 595-methionine 596 to asparagine 595-leucine 596). Such mutations are thought to cause AD by producing an increased or altered processing of APP to Aβ. In particular, the processing of APP resulting in accumulation of the longer forms of Aβ, for example, Aβ1-42 and Aβ1-43 is thought to be important in the cause of AD. Mutations in other genes, such as the presenilin genes PS1 and PS2, are thought to indirectly affect processing of APP resulting in production of the long form of Aβ. See, for example, Hardy, TINS (1997) 20:11.

It is believed that cytotoxic amyloid-beta peptide aggregates disrupt the integrity of cell membranes and elaborate reactive oxygen intermediates, thereby giving rise to elevations in cytosolic calcium and eventual cell death. Cell surface receptors for amyloid-beta peptide may also activate signal transduction mechanisms.

European Patent Publication EP 526,511 (McMichael) and PCT International Patent Publication WO/9927944 (Schenk) have described the administration of Aβ to patients for the treatment or prevention of Alzheimer's. However, although active immunization of Aβ to transgenic mice produces apparent benefits, the extension of this approach to AD patients has resulted in undesirable inflammation of the central nervous system in some of the subjects. See Hardy, D. J. Selkoe (2002) Science 297:353-356. Soluble Aβ includes Aβ monomers as well as aggregations of such monomers referred to as prefibrillar aggregates. These prefibrillar aggregates lead to the development of amyloid fibrils.

Soluble Aβ content of the human brain is better correlated with the severity of AD than is the accumulation of amyloid plaques. See, for example, Y. M. Kuo et al. (1996) J. Biol. Chem. 271:4077-4081; C. A. McLean et al. (1999) Annals of Neurology 46:860-6; L. F. Lue et al. (1999) American Journal of Pathology 155:853-862. In addition, recent reports suggest that the toxicity of Aβ and other amyloidogenic proteins lies not in the soluble monomers or insoluble fibrils that accumulate, but rather in the prefibrillar aggregates. See, for example, Hartley et al. (1999), Journal of Neuroscience 19:8876-8884; Lambert et al., PNAS (1998) 95:6448-53; and Bucciantini et al., Nature (2002) 416:507-511; and Hartley et al. Nature (2002) 418:291. Taken together, these results indicate that the prefibrillar aggregates may be more pathologically significant than other forms of the amyloid peptides and therefore may be a more desirable target in the prevention or curing of amyloid diseases such as AD.

PCT International Patent Application PCT/US2003/028829 (WO 2004/024090, US 2011/0200609) entitled "Monoclonal Antibodys And Corresponding Antibodies Specific For High Molecular Weight Aggregation Intermediates Common To Amyloids Formed From Proteins Of Differing Sequence" (Kayed and Glabe) describes compositions of matter comprising one or more conformational epitopes found on amyloid peptide aggregates, antibodies to such epitopes and methods for making and using the compositions, epitopes and/or antibodies. The compositions described in PCT/US2003/028829 include synthetic or isolated compositions that contain or consist of certain conformational epitopes found on peptide aggregates (e.g., toxic peptide aggregates) present in human or veterinary patients who suffer from, or who are likely to develop, amyloid diseases (e.g., Alzheimer's Disease). The invention described in PCT/US2003/028829 also includes methods for using such compositions in the detection, treatment and prevention of diseases in humans or animals and/or in the testing and identification of potential therapies (e.g., drug screening) using such antibodies. The entirety of PCT International Patent Application PCT/US2003/028829 is expressly incorporated herein by reference.

There remains a need for the development of agents that bind or inhibit, directly or indirectly, toxic forms of amyloid (e.g., cytotoxic amyloid-beta peptide aggregates or protofibrils) providing for diagnosis and treatment of amyloid diseases.

SUMMARY

Evidence indicates that intermediate sized aggregates of neurodegenerative disease associated proteins called oligomers (e.g., amyloid oligomers) are the true pathogenic entities, rather than larger aggregates. Aspects described herein are directed to methods and reagents directed to these oligomers.

Compositions and methods described herein can be used to identify pathogenic or potentially pathogenic conditions—for example, the detection of amyloid oligomers can be used as an early biomarker for diseases such as Alzheimer's disease. In certain aspects an oligomer specific antibody can be used to detect amyloid oligomers or treat diseases related to amyloid oligomers. The oligomer specific antibody does not significantly bind soluble amyloid beta or amyloid-beta fibrils. In a further aspect, the antibody specifically binds a conformational epitope of an oligomer and does not bind soluble amyloid beta or amyloid-beta fibrils, thus, in certain aspects, the antibodies can identify similar conformational epitopes formed by other proteins and polypeptides that contain amino acid sequences that are distinct from SEQ ID NO:1, which is described below. The term "oligomer" refers to a protein aggregate having about 3 to 24 peptides, e.g., an amyloid oligomer. The term "soluble amyloid" refers to a monomer or dimer of amyloid proteins. The term "amyloid fibril" refers to an insoluble amyloid aggregate differing in conformation (e.g., having distinct epitopes as compared to amyloid oligomer) and differing in phosphorylation status from amyloid oligomers—amyloid fibrils are more stable than amyloid oligomers.

In certain embodiments, the antibody is a monoclonal antibody or antibody fragment that specifically binds amyloid oligomers and does not bind soluble amyloid beta or amyloid-beta fibrils. Oligomer specific monoclonal antibodies described herein can be used to analyze amyloid oligomers in animal models and humans, as well as biological fluids from patients with or suspected of having amyloid related diseases such as Alzheimer's disease (AD) and many neurodegenerative diseases. The antibody can be a mouse antibody, a human antibody, or a humanized antibody. In certain aspects the antibody is a mouse monoclonal antibody. In other aspects, the antibody is formulated in a pharmaceutically acceptable formulation.

Embodiments are directed to a monoclonal antibody or an antibody fragment that specifically binds an oligomer comprising all or part of a peptide having the amino acid sequence GKHGAGAAAAGAVVGGLGGYGLGSAG-SRPIIHFGSDYEDRY (SEQ ID NO:1), including peptides that are 80, 85, 90, 95, 98, 99, or 100% identical to SEQ ID NO:1. In certain aspects the monoclonal antibody or antibody fragment that binds an oligomer comprising a peptide of SEQ ID NO:1 is a mouse monoclonal antibody or mouse antibody fragment. In a further aspect the antibody can be a single chain antibody. In certain aspects the monoclonal antibody or antibody fragment is a humanized monoclonal antibody or antibody fragment. In certain aspects the monoclonal antibody is monoclonal antibody F11G3 or F8H7 or fragments thereof. The F11G3 heavy chain variable region has an amino acid sequence of EVQLQQSGPELVKPGASVKMSCKAS-GYTFTDYYMK WVKQSHGKSLEWIGDINPNNGDT-FYNQKFKGKATLTVDKSSSTAYMQLNSLTSEDSAV YYCARGVYDGYYAMDYWGQGTSVTVSS (SEQ ID NO:11). The F11G3 light chain variable region has an amino acid sequence of DIVMTQAAPSVPVTPGESVSISCRSSK-SLLHSNGNTYLYWFLQR-PGQSPQLLIYRMSNLASGVPDR FSGSGSGTAFTLRIS-RVEAEDVGVYYCMQHLEYPLTFGAGTKLELK (SEQ ID NO:12). The monoclonal antibody or antibody fragment can comprise an amino acid sequence that is 80, 85, 90, 95, 98, or 100% identical to the amino acid sequence of SEQ ID NO:11 and/or SEQ ID NO:12. In a further aspect a monoclonal antibody or fragment thereof is comprised in a composition, such as a diagnostic or pharmaceutically acceptable composition or formulation.

In certain aspects the compositions can be used as a novel treatment for amyloid related conditions. In certain aspects antibodies of the invention can be used to reduce amyloid aggregates, or reduce or inhibit the formation of amyloid aggregates. In other aspects, a peptide or an oligomer having the amino acid sequence of SEQ ID NO:1 can be used to induce antibodies that reduce amyloid aggregates, or reduce or inhibit the formation of amyloid aggregates.

Certain aspects of the invention include methods of evaluating a patient suspected of or having an amyloid related disease comprising the step of detecting binding of an amyloid oligomer specific antibody to a component of a biological sample from the patient, wherein the detection of amyloid oligomer in the biological sample is indicative of an amyloid related disease. In certain aspects a method of evaluating a patient suspected of or having a amyloid related disease can comprise the step of detecting binding of an antibody that (a) specifically binds an oligomer comprising a peptide having the amino acid sequence of SEQ ID NO:1 and (b) specifically binds to an amyloid oligomer in a biological sample from the patient, wherein the detection of the amyloid oligomer in the biological sample is indicative of an amyloid related disease. The amyloid related disease could be Alzheimer's disease or other disease condition that is associated with amyloid oligomers. In certain aspects, an amyloid oligomer is detected by immunoassay. A biological sample includes, but is not limited to blood, plasma, serum, cerebrospinal fluid (CSF), brain tissue, neuronal tissue, or muscle tissue. In certain aspects the amyloid oligomer specific antibody comprises a detectable agent. The detectable agent can include, but is not limited to a radioactive marker, a nucleic acid, a fluorescent label, or an enzymatic label.

In yet another aspect, to the invention provides methods for treating an amyloid related disease comprising the step of administering an effective amount of a peptide comprising or consisting of the amino acid sequence of SEQ ID NO:1 or an amyloid oligomer specific antibody that specifically binds a peptide having or consisting of the amino acid sequence of SEQ ID NO:1 to a subject having or suspected of having AD or other amyloid related disease. Such a peptide or an antibody specific for the peptide can be administered at a dose of about, at least, or at most 0.1, 10, 20, 50, 100, 200 mg/kg to 20, 50, 100, 200, 500 mg/kg, including all values and ranges there between. The peptide or antibody can be administered into the blood or CSF. Due to the conformational specificity of the antibodies described, amyloid related diseases that can be treated with these methods include, but are not limited to Alzheimer's disease (Beta amyloid), Type 2 diabetes mellitus (IAPP (Amylin)), Parkinson's disease (Alpha-synuclein), Transmissible spongiform encephalopathy (Prion), Huntington's Disease (Huntingtin), Medullary carcinoma of the thyroid (Calcitonin), Cardiac arrhythmias (Atrial natriuretic factor), Atherosclerosis (Apolipoprotein AI), Rheumatoid arthritis (Serum amyloid A), Aortic medial amyloid (Medin), Prolactinomas (Prolactin), Familial amyloid polyneuropathy (Transthyretin), Hereditary non-neuropathic systemic amyloidosis (Lysozyme), Dialysis related amyloidosis (Beta 2 microglobulin), Finnish amyloidosis (Gelsolin), Lattice corneal dystrophy (Keratoepithelin), Cerebral amyloid angiopathy (Beta amyloid), Cerebral amyloid angiopathy (Icelandic type) (Cystatin), systemic AL amyloidosis (Immunoglobulin light chain AL), or Sporadic Inclusion Body Myositis (S-IBM). In certain aspects, a peptide or an oligomer comprising a peptide of SEQ ID NO:1 is used to induce an immune response to treat an amyloid related disease (e.g., AD) or ameliorate symptoms of an amyloid related disease.

In other aspects, methods of treating an amyloid related disease or inducing an immune response to an immunogen comprising an amino acid sequence of SEQ ID NO:1 comprises administering an effective amount of a peptide or antigen composition to a subject having or suspected of having an amyloid related disease. In other aspects, passive immunotherapy can be used in treating amyloid diseases or conditions.

As used herein "passive immunity" refers to any immunity conferred upon a subject by administration of immune effectors including cellular mediators or protein mediators (e.g., monoclonal and/or polyclonal antibodies). A monoclonal or polyclonal antibody composition may be used in passive immunization for the treatment of an amyloid related disorder. An antibody composition may include antibodies that bind specifically to amyloid oligomers, particularly those antibodies generated to an oligomer of peptides having an amino acid sequence of SEQ ID NO:1. The antibody component can be a polyclonal antiserum. In certain aspects, the antibody or antibodies are affinity purified from an animal or second subject that has been challenged with an antigen(s). In other aspects, the antibodies are monoclonal antibodies, and in some aspects, the monoclonal antibodies are mouse or humanized monoclonal antibodies.

DEFINITIONS

The term "antibody", as used herein, broadly refers to any immunoglobulin (Ig) molecule or amyloid oligomer binding peptide derived from an antibody including any functional fragment, mutant, variant, or derivation thereof, which retains the essential epitope binding or amyloid oligomer binding features of an Ig molecule that specifically binds the peptide or the amyloid oligomer. Such mutant, variant, or derivative antibody formats are known in the art. In certain aspects, an antibody is a monoclonal antibody or a single chain antibody. In still further aspects, the antibody is a recombinant antibody segment that retains amyloid oligomer specific binding. Typically, antibody fragments compete with the intact antibody from which they were derived for specific binding to an antigen. Fragments include separate heavy chains, light chains Fab, Fab' F(ab')2, Fabc, and Fv. Fragments are produced by recombinant DNA techniques, or by enzymatic or chemical separation of intact immunoglobulins.

An "isolated antibody", as used herein, is intended to refer to an antibody that is substantially free of other antibodies having different antigenic specificities.

As used herein, the term "humanized antibody" is an antibody or a variant, derivative, analog or segment thereof that immunospecifically binds to an antigen of interest and that comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, 85%, 90%, 95%, 98% or 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain.

As used herein, the term "antigen" is a molecule capable of being bound by an antibody or T-cell receptor. An antigen is additionally capable of inducing a humoral immune response and/or cellular immune response leading to the production of B- and/or T-lymphocytes. B-lymphocytes respond to foreign antigenic determinants via antibody production, whereas T-lymphocytes mediate cellular immunity. The structural aspect of an antigen, e.g., three dimensional conformation or modification (e.g., phosphorylation), which gives rise to a biological response is referred to herein as an "antigenic determinant" or "epitope." Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and usually at least 5 or 8-10 amino acids in a unique spatial conformation. Methods of determining spatial conformation of epitopes include those methods described in Epitope Mapping Protocols (1996). T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion. In certain aspects, a peptide having an amino acid sequence of SEQ ID NO:1 is used an antigen, in particular oligomers comprising SEQ ID NO:1.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a subject or a donor subject. A donor subject is one in which an antibody is generated and isolated, the isolated antibody is then administered to a second subject. Treatment or therapy can be an active immune response induced by administration of an immunogen or a passive therapy affected by administration of antibody, antibody-containing material, or primed T-cells.

The phrase that an antibody or molecule "specifically binds" or is "specifically immunoreactive" to a target refers to a binding reaction that is determinative of the presence of the target or a target containing a binding determinant in the presence of a heterogeneous population of other molecules or sample components. Thus, under designated immunoassay conditions, a specified molecule binds preferentially to a particular target and does not bind in a significant amount to other biologics or moieties present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988), for a description of immunoassay formats and conditions that can be used to determine specific immunoreactivity. Specific binding between two entities means an affinity of at least $10^6$, $10^7$, $10^8$, $10^9$ M$^{-1}$, or $10^{10}$ M$^{-1}$. Affinities greater than $10^8$ M$^{-1}$ are preferred.

"Prefibrillar aggregates", "micellar aggregates", "high molecular weight aggregation intermediates," "high molecular weight amyloid peptide aggregates", "high molecular weight soluble amyloid peptide aggregates" "amyloid peptide aggregates", "soluble aggregate intermediates", "amyloid oligomeric intermediates", "oligomeric intermediates"

and "oligomeric aggregates" or simply, "intermediates" refer to aggregations that include more than three individual peptide or protein monomers, for example, more than four peptide or protein monomers. Prefibrillar aggregates include aggregations of oligomers that form spherical structures or micelles and strings of micelles that lead to fibril formation. The molecular weight of a prefibrillar aggregate may be in a range of about 10 kDa to about 100,000,000 KDa, for example, about 10 kDa to about 10,000,000 or 1,000,000 KDa. However, this size range is not intended to be limiting and prefibrillar aggregates are not defined by a molecular weight range.

"Annular protofibrils" are a particular subset of prefibrillar aggregates in which 3 to 10 spherical oligomer subunits are arranged in an annular or circular fashion with a hollow center that appears as a pore in electron or atomic force micrographs.

"Protofibrils" are prefibrillar aggregates that include spherical structures comprising amyloid peptides that appear to represent strings of the spherical structures forming curvilinear structures.

The terms "inhibiting," "reducing," or "preventing," or any variation of these terms, when used in the claims and/or the specification includes any measurable decrease or complete inhibition to achieve a desired result, e.g., a reduced pathogenic activity of amyloid oligomers.

The use of "a" or "an" when used in conjunction with the term "comprising" in the claims and/or the specification encompasses "one or more" unless context dictates otherwise.

Throughout this application, the term "about" is used to indicate that a value includes the standard deviation of error for the method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. Furthermore, compositions and kits of the invention can be used to achieve methods of the invention. It should be understood, however, that the detailed description and the specific examples, while indicating specific embodiments of the invention, are given by way of illustration only, since various changes and modifications within the spirit and scope of the invention will become apparent to those skilled in the art from this detailed description. The embodiments in the Example section are understood to be embodiments of the invention that are applicable to all aspects of the invention. Any embodiment discussed with respect to one aspect of the invention applies to other aspects of the invention as well and vice versa.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
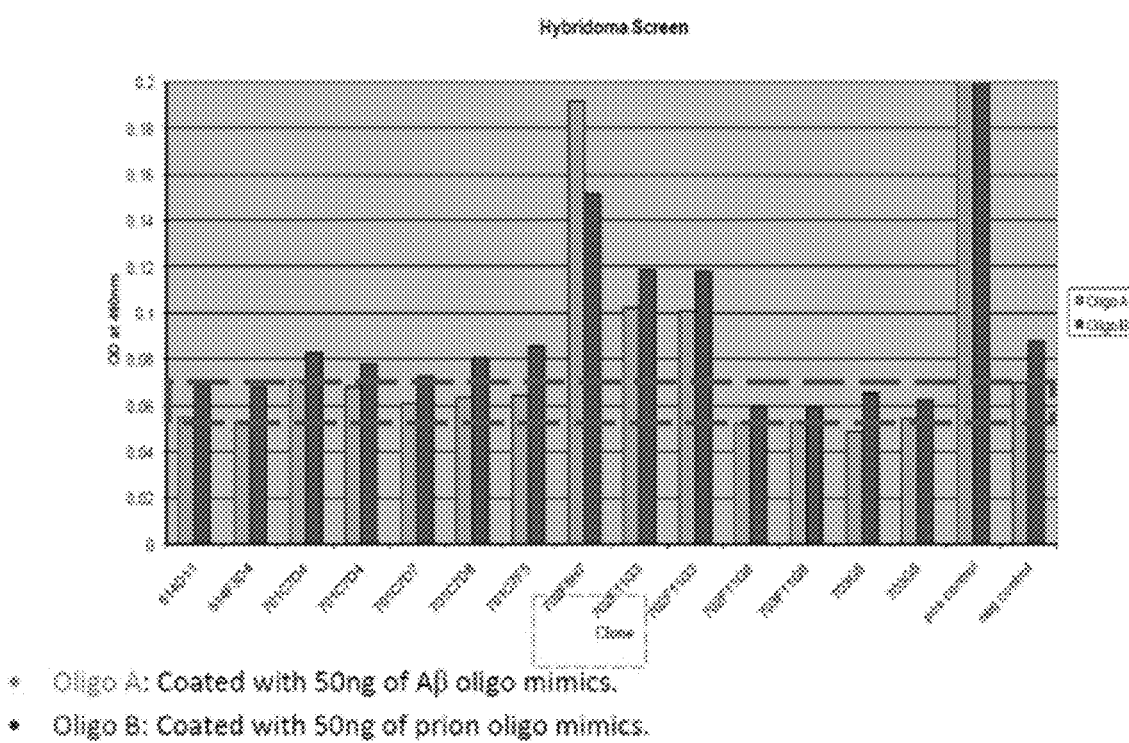
FIG. 1. Screening hybridoma clone cell culture medium. The primary screening was made by ELISA and clones showing the highest titer were expanded. ELISA plates A: Coated with 50 ng of Aβ oligo mimics. Elisa plates B: Coated with 50 ng of hPrP 109-149 oligo mimics. Similar results were obtained in the secondary screen that was performed using plates coated with 50 ng of 10 different oligomers: 3 oligo mimics and 7 natural oligomers. Oligo mimics: Aβ40, IAPP and hPrP 109-149. Natural oligomers: Aβ 40; Aβ42; IAPP, Synuclein, hPrP 109-149, Insulin, Light chain.

Pathological aggregation of the amyloid beta proteins and peptides are defining histopathological features of many neurodegenerative diseases, including Alzheimer's disease (AD). Embodiments of the invention include compositions and methods for producing and using antibodies that bind specifically to amyloid oligomers—in particular antibodies that specifically bind to a peptide having the amino acid sequence of SEQ ID NO:1. Other aspects of the invention are directed to methods of evaluating and/or treating amyloid related diseases. Embodiments relate to novel antibodies and compositions that can be employed in the treatment of a group of disorders and abnormalities associated with amyloid protein, such as Alzheimer's disease, and of diseases or conditions associated with amyloid-like proteins. Certain aspects further relate to pharmaceutical compositions comprising these antibodies or peptides, and to the use of these compositions for the preparation of medicaments for the treatment of diseases or conditions associated with amyloid or amyloid-like proteins. A method of treating amyloidosis and diseases or conditions associated with amyloid or amyloid-like proteins is also disclosed.

Alzheimer's Disease (AD) is a neurological disorder characterized by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques is associated with nerve cell death, which contributes to the development and progression of AD. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP) by the enzymes β and γ secretase leads to the release of a 39 to 43 amino acid Aβ peptide. The degradation of APPs likely increases their propensity to aggregate in plaques.

Presently, the only definite way to diagnose AD is to identify plaques and tangles in brain tissue in an autopsy after death of the individual. Therefore, doctors can only make a diagnosis of "possible" or "probable" AD while the person is still alive.

As discussed herein, a number of diseases are associated with protein aggregation. Each of the following peptides have been shown to form peptide aggregates that are recognized by antibodies produced against oligomers of peptides having an amino acid sequence of SEQ ID NO:1, thus there is a common conformational epitope that is recognized by the antibodies described herein. Thus, certain aspects are related to methods and compositions of various peptide or protein sequences which form aggregates associated with other diseases, such as: A40 (DAEFRHDSGYEVHHQKLVFFAEDVGSNKGAI IGLMVGGVV) (SEQ ID NO:2), A42 (DAEFRHDSGYEVHHQKLVFFAEDVGSNKG AIIGLMVGGVVIA) (SEQ ID NO:3), Human IAPP (KCNTATCATQRLANFLVHSS NNFGAILSSTNVGSNTY) (SEQ ID NO:4), and Human Prion 106-126 (KTNMKHMAGAAAAGAVVGGLG) (SEQ ID NO:5).

Stefani and coworkers (Bucciantini et at (2002) Nature 416, 507-511) have recently reported that amyloid peptide aggregates formed from non-disease related proteins are inherently cytotoxic, suggesting that they may have a structure in common with disease related amyloid peptides. Non-disease related amyloid peptides are Poly glutamine synthetic peptide KK(Q40)KK (KKQQQQQQQQQQQQQQQQQQQQQQQQQQQQ QQQQQQQQQQQQKK) (SEQ ID NO:6), Human Lysozyme (MKALIVLGLV LLSVTVQGKVFER-CELARTLKRLGMDGYRGSLANWMCLAK-WESGYNTRATNYNAGD RSTDYGIFQINSRY-WCNDGKTPGAVNACHLSCSALLQDNIADAVACAK RVVRD PQGIRAWVAWRNRCQNRDVRQYVQGCGV) (SEQ ID NO:7), Human Insulin (MALWMRLLPLLALLA-LWGPDPAAAFVNQHLCG-SHLVEALYLVCGERGFFYTPKTRRE AEDLQVGQVEL-GGGPGAGSLQPLALEGSLQKRGIVEQCCTSICSLY QLENYCN) (SEQ ID NO:8), Human Transthyretin (MASHRLLLLCLAGLVFVSEAGPTGTGESKC PLM-VKVLDAVRGSPAINVAVHVFRKAAD-DTWEPFASGKTSESGELHGLTTEEEFVEGIY KVEIDTKSYWKALGISPFHEHAEV-VFTANDSGPRRYTIAALLSPYSYSTTAVVTNPKE) (SEQ ID NO:9), and Human Alpha Synuclein (MD-VFMKGLSKAKEGVVAAAE KTKQGVAEAAGKTKEG-VLYVGSKTKEGVVHGVATVAEKTKEQVT-NVGGAVVTGVTA VAQKTVEGAGSIAAATG-FVKKDQLGKNEEGAPQEGILEDMPVDPD-NEAYEMPSE EGYQDYEPEA) (SEQ ID NO:10).

I. Polypeptide or Peptide Compositions

Certain embodiments are related to peptides, oligomers, antibodies, and antibody fragments for use in various embodiments of the present invention. For example, antibodies generated to a peptide or oligomers comprising a peptide having an amino acid sequence of SEQ ID NO:1 are identified for specific binding to amyloid oligomers.

A. Anti-Oligomer Antibodies

Certain embodiments of the invention are directed to antibodies that specifically bind an oligomer comprising a peptide having the amino acid sequence of SEQ ID NO:1 and specifically bind amyloid oligomers. In certain aspects the invention is directed to mouse monoclonal antibodies that specifically bind the peptide having the amino acid sequence of SEQ ID NO:1 and humanized versions of these mouse monoclonal antibodies.

To generate antibodies an immunostimulatory amount of inoculum is administered to a mammal and the inoculated mammal is then maintained for a time sufficient for the antigenic composition to induce protective antibodies. The antibodies can be isolated to the extent desired by well-known techniques such as affinity chromatography (Harlow and Lane, 1988). Antibodies can include antiserum preparations from a variety of commonly used animals e.g., goats, primates, donkeys, swine, horses, guinea pigs, rats or man. The animals are bled and serum recovered.

Inocula for polyclonal antibody production are typically prepared by dispersing the antigenic composition (e.g., a peptide or oligomer comprising a peptide(s) having an amino acid sequence of SEQ ID NO:1) in a physiologically tolerable diluent such as saline or other adjuvants suitable for human use to form an aqueous composition.

Antibodies to the antigen are subsequently collected from the sera of the host. The polyclonal antibody can be affinity purified against the antigen rendering it monospecific. An antigen composition of the present invention can be administered to a recipient who then acts as a source of antibodies, produced in response to challenge an antigen composition comprising a peptide having the amino acid sequence of SEQ ID NO:1. A subject thus treated would donate plasma from which antibody would be obtained via conventional plasma fractionation methodology; or would donate antibody producing cells that could be cultured and used for production of antibodies in culture. In other aspects, the gene encoding an amyloid oligomer specific antibody can be cloned, and antibody produced by recombinant methods. The isolated antibody would be administered to the same or different subject in order to impart resistance against or treat an amyloid related disease or condition. In order to produce polyclonal antibodies, a host, such as a rabbit or goat or human, is immunized with the antigen or antigen segment, generally with an adjuvant and, if necessary, coupled to a carrier.

In order to produce monoclonal antibodies, hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then cultured, in bulk, and the monoclonal antibodies harvested from the culture media for use. By definition, monoclonal antibodies are specific to a single epitope (e.g., amyloid oligomers). Monoclonal antibodies often have lower affinity constants than polyclonal antibodies raised against similar antigens for this reason.

Monoclonal antibodies may also be produced ex vivo by use of primary cultures of splenic cells or cell lines derived from spleen (Anavi, 1998). In order to produce recombinant antibody (see generally Huston et al., 1991; Johnson et al., 1991), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries. Alternatively, monoclonal Fv fragments can be obtained by screening a suitable phage display library (Vaughan et al., 1998). Monoclonal antibodies may be humanized or part humanized by known methods.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Typically, antibodies are comprised of four polypeptide chains, two heavy (H) chains and two light (L) chains. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyterminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgAI and IgA2) or subclass.

The framework and CDR regions of an antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences.

Certain embodiments are directed to anti-oligomer antibodies that specifically bind cytotoxic oligomers, are conformation-dependent, do not bind native precursor or monomer, and/or do not bind fibrils or plaques. In certain aspects, the antibodies are generated by vaccinating mice or other animal host with oligomers comprising peptide AG712. AG712 has a sequence that is rich with Alanine and Glycine. The amino acid sequence of AG712 is GKHGAGAAAAGAVVGGLG-GYGLGSAGSRPIIHFGSDYEDRY (SEQ ID NO:1).

B. Peptide Compositions

In certain embodiments, all or part of the peptides or proteins of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide of the invention is inserted into an expression vector, transformed or transfected into an appropriate host cell and cultivated under conditions suitable for expression.

In a certain aspects, an immunogenic composition according to the invention comprises a peptide that has at least 85% identity, at least 90% identity, at least 95% identity, or at least 97-99% identity, including all values and ranges there between, to a peptide having a sequence of SEQ ID NO:1.

It will be understood that amino acid and nucleic acid sequences may include additional residues, such as additional N- or C-terminal amino acids, or 5' or 3' sequences, respectively, and yet still be essentially as set forth in one of the sequences disclosed herein (e.g., SEQ ID NO:1). The addition of terminal sequences particularly applies to nucleic acid sequences that may, for example, include various non-coding sequences flanking either of the 5' or 3' portions of the coding region.

The following is a discussion based upon changing of the amino acids of a protein or peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules (e.g., antigenic determinants or epitopes). Since it is the interactive capacity and nature of a protein that defines that protein's biological functional activity, certain amino acid substitutions can be made in a protein or peptide sequence, and in its underlying DNA coding sequence, and nevertheless produce a protein or peptide with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

II. Therapeutic and Diagnostic Methods

Certain methods include treatment for or diagnosis of an amyloid related disease or condition caused by amyloid oligomers. Furthermore, in some examples, treatment comprises administration of other agents commonly used to treat amyloid related disease. Therapeutic and diagnostic aspects of the invention include antibodies that specifically bind to amyloid oligomers via either sequence specific or conformation specific epitope(s). The present invention provides for amyloid disease therapeutics that can induce a specific immune response against amyloid oligomers or provide passive immunity to amyloid oligomers.

One use of the immunogenic compositions of the invention is to prophylactically treat a subject in early stages of an amyloid related disease by inoculating a subject, particularly once a risk of developing an amyloid related disease has been indicated. In certain aspects, a "risk" means symptoms being presented or having a familial history of an amyloid related disease, i.e., a genetic predisposition.

Such prophylactic therapy can be imparting a passive immunity to the subject. Passive immunity may be imparted to a patient or subject by administering to the patient immunoglobulins (Ig) or fragments thereof and/or other immune factors obtained from a donor or other non-patient source having a known immunoreactivity. In other aspects recombinantly produced antibodies can also be used to confer passive immunity. In other aspects, an antigenic composition of the present invention can be administered to a subject who then acts as a source or donor for globulin, produced in response to challenge from the composition ("hyperimmune globulin"), that contains antibodies directed against amyloid oligomers. A subject thus treated would donate plasma from which hyperimmune globulin would then be obtained, e.g., via conventional plasma-fractionation methodology, and administered to another subject in order to impart resistance against or to treat an amyloid related disease. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

The compositions and related methods of the present invention, particularly administration of an immunogenic composition comprising a peptide or an oligomer comprising a peptide(s) comprising or consisting of an amino acid sequence of SEQ ID NO:1 or an antibody that specifically binds an oligomer of SEQ ID NO:1 and/or amyloid oligomers to a patient/subject, may also be used in combination with the administration of traditional therapies.

In one aspect, it is contemplated that a traditional therapy is used in conjunction with a composition comprising an oligomer comprising or consisting of an amino acid sequence of SEQ ID NO:1 or an amyloid oligomer specific antibody treatment. Alternatively, the therapy may precede or follow the traditional therapy by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example immunogenic compositions or amyloid oligomer specific antibody therapy is a first therapeutic agent and a traditional amyloid related disease therapy is a second therapeutic agent. The two or more therapeutic agents can be co-formulated, or they can be separately formulated and co-administered simultaneously or consecutively in any order. Therapeutics that restore the deficit (defect), or malfunctioning, in the chemical messengers of the nerve cells (neurotransmitters), in particular the cholinesterase inhibitors (ChEIs) such as tacrine and rivastigmine, have been shown to improve symptoms of amyloid related diseases. ChEIs impede the enzymatic degradation of neurotransmitters thereby increasing the amount of chemical messengers available to transmit the nerve signals in the brain.

In certain aspects, anti-oligomer antibodies of the invention can be used to detect the effects of small molecules on the persistence or diminution of oligomers in high-through put screening assays.

Compositions of the invention can be used to characterize oligomeric species in human brain, serum, CSF and transgenic animals.

Certain aspects in the use of the antigen include a vaccine specifically targeting toxic amyloid oligomers. Furthermore, the anti-oligomer antibodies can be provided as a passive immunotherapy, intrabodies, humanized mAb agents for the detection and/or treatment of amyloid related diseases.

In particular aspects, the anti-oligomer antibodies can be used in producing early diagnostic kits.

The antibodies described herein can be used in immuno-histochemical and biochemical methods in combination with other well characterized antibodies for qualitative and quantitative analysis of the oligomer levels, localization and posttranslational modifications of oligomers in brain samples and CSF samples using direct ELISA, immunoprecipitation/western, and sandwich ELISA.

Anti-oligomer antibodies can be used in transgenic animal models for assessment of therapeutic efficacy. For example, amyloid oligomers can be studied in brain from the AD models Tg 2576 and APP/PS1 mice, as well as the P301L amyloid (JNPL3).

Many diseases of aging are based on or associated with amyloid or amyloid-like proteins and are characterized, in part, by the build-up of extracellular deposits of amyloid or amyloid-like material that contribute to the pathogenesis, as well as the progression of the disease. These diseases, include, but are not limited to, neurological disorders such as Alzheimer's Disease (AD), mild cognitive impairment (MCI), Lewy body dementia, Down's syndrome, hereditary cerebral hemorrhage with amyloidosis (Dutch type), and the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes; senile cardiac amyloidosis; endocrine tumors, and other diseases, including amyloid-associated ocular diseases that target different tissues of the eye, such as the visual cortex, including cortical visual deficits; the anterior chamber and the optic nerve, including glaucoma; the lens, including cataract due to beta-amyloid deposition; the vitreous, including ocular amyloidoses; the retina, including primary retinal degenerations and macular degeneration, in particular age-related macular degeneration; the optic nerve, including optic nerve drusen, optic neuropathy and optic neuritis; and the cornea, including lattice dystrophy.

III. Administration and Formulation

As discussed above, the compositions can be administered to a subject having, suspected of having, or at risk of developing an amyloid related disease. Therapeutic compositions are administered in a manner compatible with the dosage formulation, and in such amount as will be therapeutically effective. The quantity to be administered depends on the subject to be treated. Precise amounts of active ingredient to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide as a therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject. Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain aspects an amyloid oligomer specific antibody that specifically binds an oligomer comprising a peptide having an amino acid sequence of SEQ ID NO:1 can be administered into the cerebrospinal fluid of the brain or spine. In certain embodiments, an immunogenic composition of the invention may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

In certain instances, it will be desirable to have multiple administrations of the composition, e.g., 2, 3, 4, 5, 6 or more administrations. The administrations can be at 1, 2, 3, 4, 5, 6, 7, 8 to 5, 6, 7, 8, 9, 10, 11, 12 day or week intervals, including all ranges there between.

Administration of the antibody or immunogenic compositions of the present invention to a patient/subject will follow general protocols for the administration of such compositions, taking into account the toxicity, if any, of the composition. It is expected that the treatment cycles would be repeated as necessary. It is also contemplated that various standard therapies, such as hydration, may be applied in combination with the described therapy.

In some embodiments, pharmaceutical compositions are administered to a subject to treat amyloid related disease or condition. Alternatively, an expression vector encoding one or more such antibodies or polypeptides or peptides may be given to a patient as a treatment. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds of the present invention can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified. The form should be sterile and should be fluid to the extent that it may be easily injected. It also should be stable under the conditions of manufacture and storage and can be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization (e.g., filter sterilization) or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterilized solution thereof.

A pharmaceutical composition comprising antibodies that specifically bind an oligomer comprising a peptide having an amino acid sequence of SEQ ID NO:1 and/or amyloid oligomers and a pharmaceutically acceptable carrier is a further aspect of the invention that can be used in the manufacture of a medicament for the treatment or prevention of an amyloid related disease or condition.

An additional aspect of the invention is a pharmaceutical composition comprising one of more antibodies or monoclonal antibodies (or fragments thereof; preferably human or humanized) generated by using peptides having an amino acid sequence of SEQ ID NO:1 that specifically bind amyloid oligomers. It is contemplated that in compositions of the invention, there is about 0.001, 0.01, 0.1, 1, 5, µg or mg to about 0.01, 0.1, 1, 5, 10 µg or mg of total polypeptide, peptide, and/or protein per ml. The concentration of protein in a composition can be about, at least about or at most about 0.001, 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml, including all values and ranges there between. In certain aspects the dose range is 0.01 to 500 mg/kg, 10 to 300 mg/kg, or 0.01 to 10 mg/kg. About, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a peptide having the amino acid sequence of SEQ ID NO:1 or antibody that specifically binds the same.

An effective amount of therapeutic or prophylactic composition is determined based on the intended goal, i.e., treatment or amelioration of an amyloid related disease. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. Examples

The following examples as well as the figures are included to demonstrate certain embodiments of the invention. It should be appreciated by those of skill in the art that the techniques disclosed in the examples or figures represent techniques discovered by the inventors to function well in the practice of the invention, and thus can be considered to constitute modes for its practice. However, those of skill in the art should, in light of the present disclosure, appreciate that changes can be made in the specific embodiments disclosed and still obtain a like or similar result without departing from the spirit and scope of the invention.

In one example, studies were performed with BALB/c mice. The mice were administered 20-25 µg of AG712 antigen per 100 µl by subcutaneous injection at multiple sites. The antigen was emulsified in Freund's adjuvant. The initial injection was followed by at least 2 more administrations of antigen approximately 3 weeks apart. Seven to ten days after a 3rd administration of the antigen animals were boosted with daily injection for 4 days, with antigen in saline, intraperitoneal. Titer was determined using limiting dilutions in ELISA. Mice were bled on day 7 after the 3rd administration. After bleeding, the animals were sacrificed and spleens collected for monoclonal antibody production.

Antibodies were Subjected to a Primary Screening for Anti-Oligomer (A).

The screen included Elisa plates A: Coated with 50 ng of Aβ oligo mimics; Elisa plates B: Coated with 50 ng of hPrP 109-149 oligo mimics; Elisa plates C: Coated with 50 ng of 10 different oligomers: 3 oligo mimics and 7 natural oligomers $AB_{40}$, $AB_{42}$, IAPP, synuclein, $hPrp_{109-149}$. Dot blot strips were also prepared having Aβ soluble, Aβ oligomer, Aβ fibrils, synuclein oligomers, and IAPP oligomers. These studies identified various anti-oligomer sub-clones including 2/5 G8, 4/3 G11, 4/3 F12, 4/3 G1, 4/3 D2, 3/4 G11 3/1 C5, 3/1 G12, 5/1 G5, 5/1 G11, 5/1 F5, 5/1 D5, 5/1 E6, 5/1 E9, 5/3 F5, and 5/3 D5. (See FIG. 1 for anti-oligomer screening data)

The clones identified in the primary screen were then subjected to a secondary screen that included: Western blot, (using in vitro prepared samples); immunohistochemistry (IHC), in human tissues and mouse models; Western using tissue homogenates; ELISA using biological fluids cerebrospinal fluid (CSF) and blood; Functional (prevention of toxicity in cells); and passive vaccination in mice.

As a result of these screens anti-oligomer monoclonal antibodies F8H7 and F11G3 were identified, characterized, and produced. Also in production are hybridoma cells producing F8H7(H3): IgM growing in serum free; F8H7(H3): IgG2a growing in serum free; F11G3 (A4): IgM growing in serum free; and F11G3 (A4): IgG2a growing in 10% serum.

Figure 2:
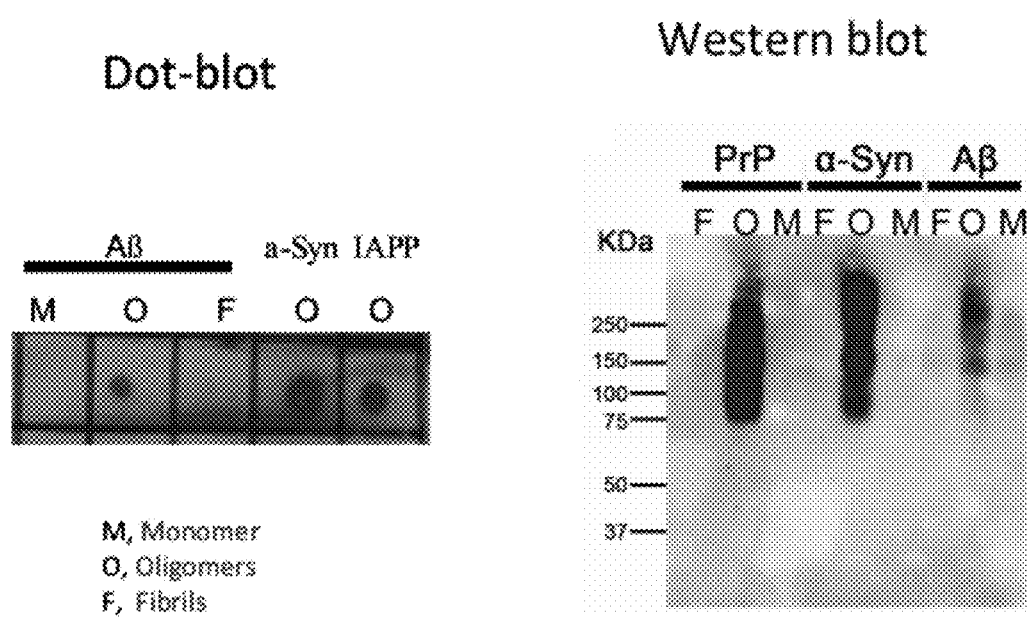
FIG. 2 Specificity of anti-oligomer mouse monoclonal antibody. (A) Dot blot using anti-oligomer antibody (F11G3) against Aβ monomer (Aβ M), oligomer (Aβ O), fibrils (Aβ F), α-synuclein oligomers (α-Syn O), amylin (IAPP). (B) Western blot using the same antibody PrP fibrils (PrP F), oligomers (PrP O), monomer (PrP M), α-synuclein fibrils (α-Syn F), oligomers (α-Syn O), monomer (α-Syn M), Aβ fibrils (Aβ F), Aβ oligomer (Aβ O), Aβ monomer (Aβ M). It is clear that that the mouse monoclonals developed are oligomer specific and do not recognize monomer proteins or amyloid fibrils.
Figure 3:
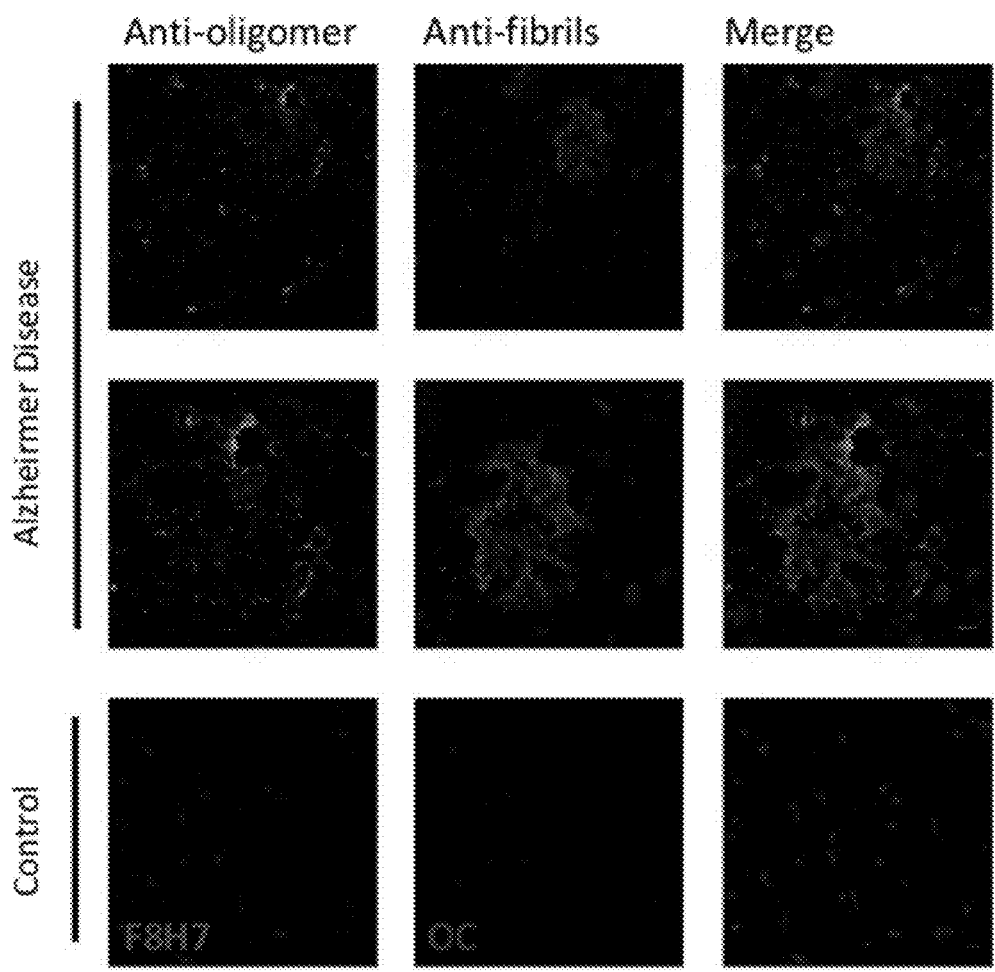
FIG. 3 Immunofluorescence micrographs of human brain tissue. AD brain and age matched control were immunostained with oligomer-specific antibody (F11G3) and counterstained with the fibrillar specific antibody OC (Kayed et al Molecular neurodegeneration 2007). This shows that F11G3 is specific for amyloid oligomers and does not recognize fibrils in vivo.

Anti-oligomer antibody specificity is demonstrated by dot blotting against Aβ monomer, oligomer, and fibril; synuclein oligomer; and IAPP oligomer. Anti-oligomer antibody specificity is also demonstrated by western blotting of tissue homogenates containing PrP, synuclein, and Aβ. (FIG. 2)

Selected Anti-Oligomer Antibodies can Detect Oligomers in AD Brain.

Figure 4:
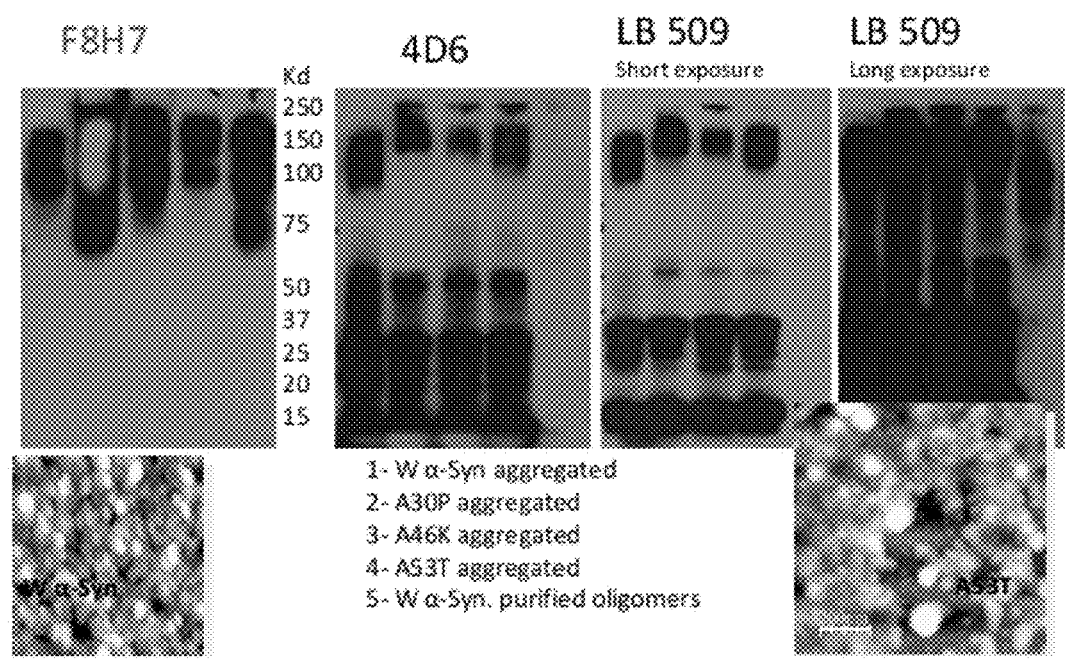
FIG. 4 Western blot analysis of aggregated wild type α-synuclein and α-synuclein with the PD associated mutations, using the novel conformation specific anti-oligomers mouse monoclonal F8H7, and commercially available anti-α-synuclein antibodies 4D6 and LB5095. It is clear that our antibody F8H7 does not recognize monomeric α-synuclein or the fibrillar material on top of the gel. It specifically recognizes α-synuclein oligomers. At the bottom Atomic Force Images of wild type α-synuclein and mutant α-synuclein with A53T mutation showing the morphology of the α-synuclein oligomers recognized by F8H7, these resemble the oligomers implicated with PD.
Figure 5:
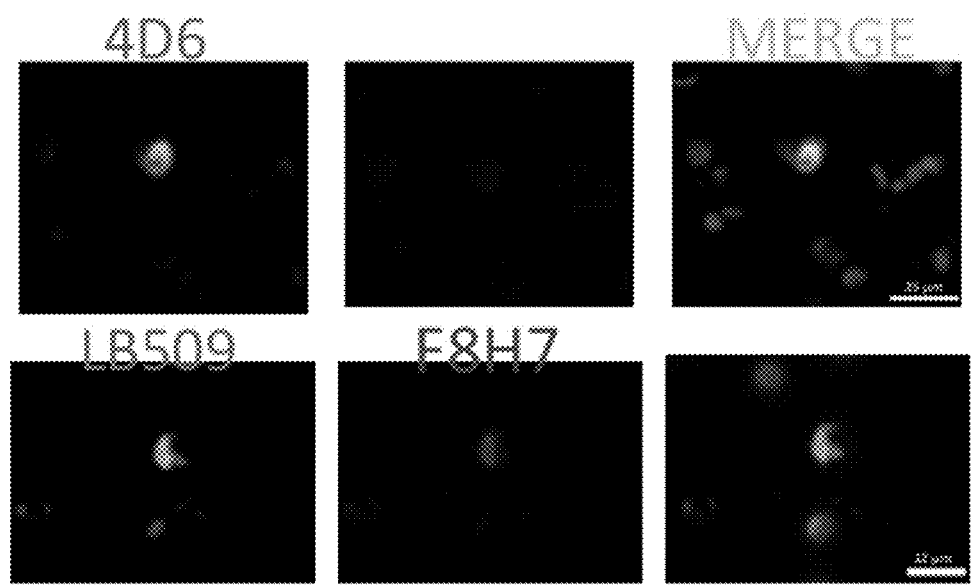
FIG. 5 α-synuclein oligomers in PD brain using F8H7; it is clear that all Lewy bodies contain α-synuclein, still only a fraction; especially immature ones contain α-synuclein oligomers.
Figure 6:
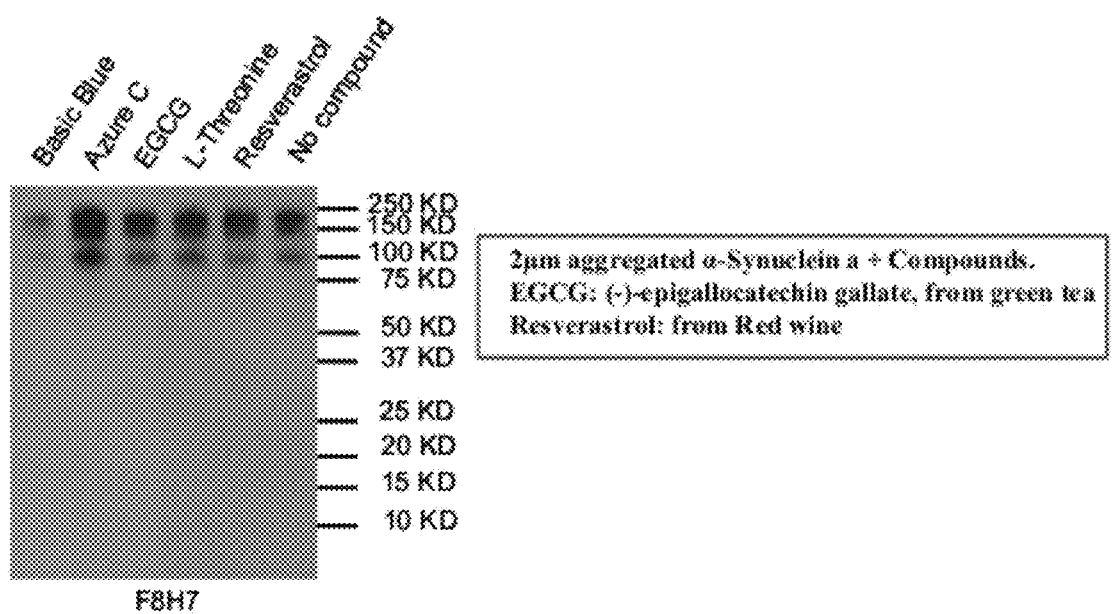
FIG. 6 The antibodies described here can be used to screen for small molecules capable of interfering with protein aggregation. Western blot analysis of α-synuclein incubated alone (no compound) and incubated with different small molecules. The western blot using F8H7, show that while three of the five compounds have no effect of α-synuclein aggregation, Azure C can accelerate the formation of α-synuclein oligomers, while Basic Blue can prevent their formation. Similar results were obtained when the samples were analyzed by ELISA.
Figure 7:
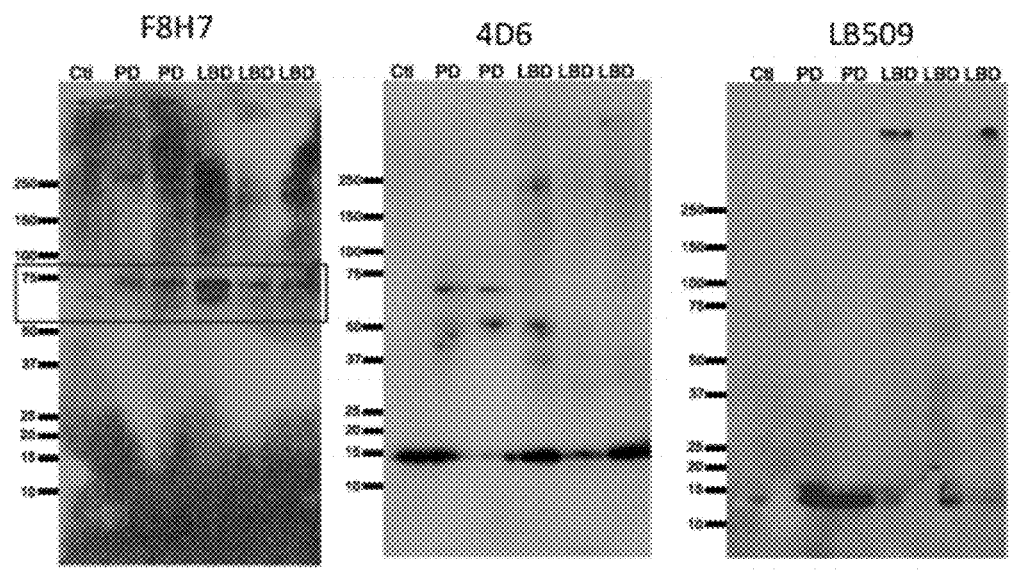
FIG. 7 Western blot analysis of PBS homogenates of frontal cortex samples from of PD & Dementia with Lewy bodies (DLB) human brains. F8H7 revealed the presence of elevated levels of α-synuclein oligomers in frontal cortex of PD & DLB patients compared to control brain samples. Reaffirming the hypothesis that oligomers play a role in PD and DLB, and the potential for F8H7 to be developed into a vaccine.

Also, anti-oligomer antibodies (e.g., F8H7) can specifically detect synuclein oligomers (FIG. 2) on western blot of Parkinson's disease and LBD brain, and in Parkinson's disease brain sections (FIG. 4).

The Efficacy of Passive or Active Vaccination can be Assessed Using Anti-Oligomer Antibodies in Transgenic Mouse Models.

Figure 8:
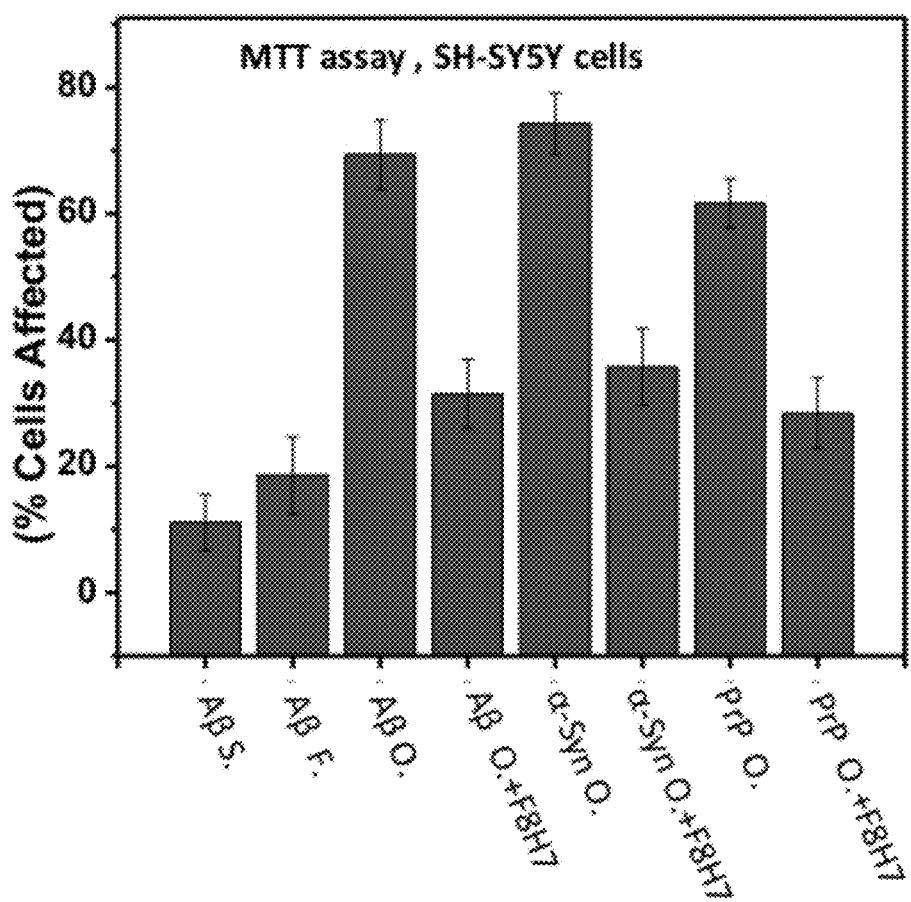
FIG. 8 Oligomers are the most toxic form of amyloid. Aβ monomer (Aβ S), fibrils (Aβ F), were not toxic while and oligomer (Aβ O) were highly toxic, same is true for α-synuclein oligomers (α-Syn O), and prion oligomers (PrP O), The toxicity of all types of oligomers was eliminated by anti-oligomer specific antibody F8H7. The toxicity was evaluated using SH-SY5Y human neuroblastoma cells and cells viability was assessed spectrophotometrically using an MTT (3-[4,5-dimethylthiazol-2-yl]-2,5-diphenyl tetrazolium bromide)-based standard assay FIG. 9 A schematic illustrating the central role of amyloid oligomers in degenerative diseases.
Figure 9:
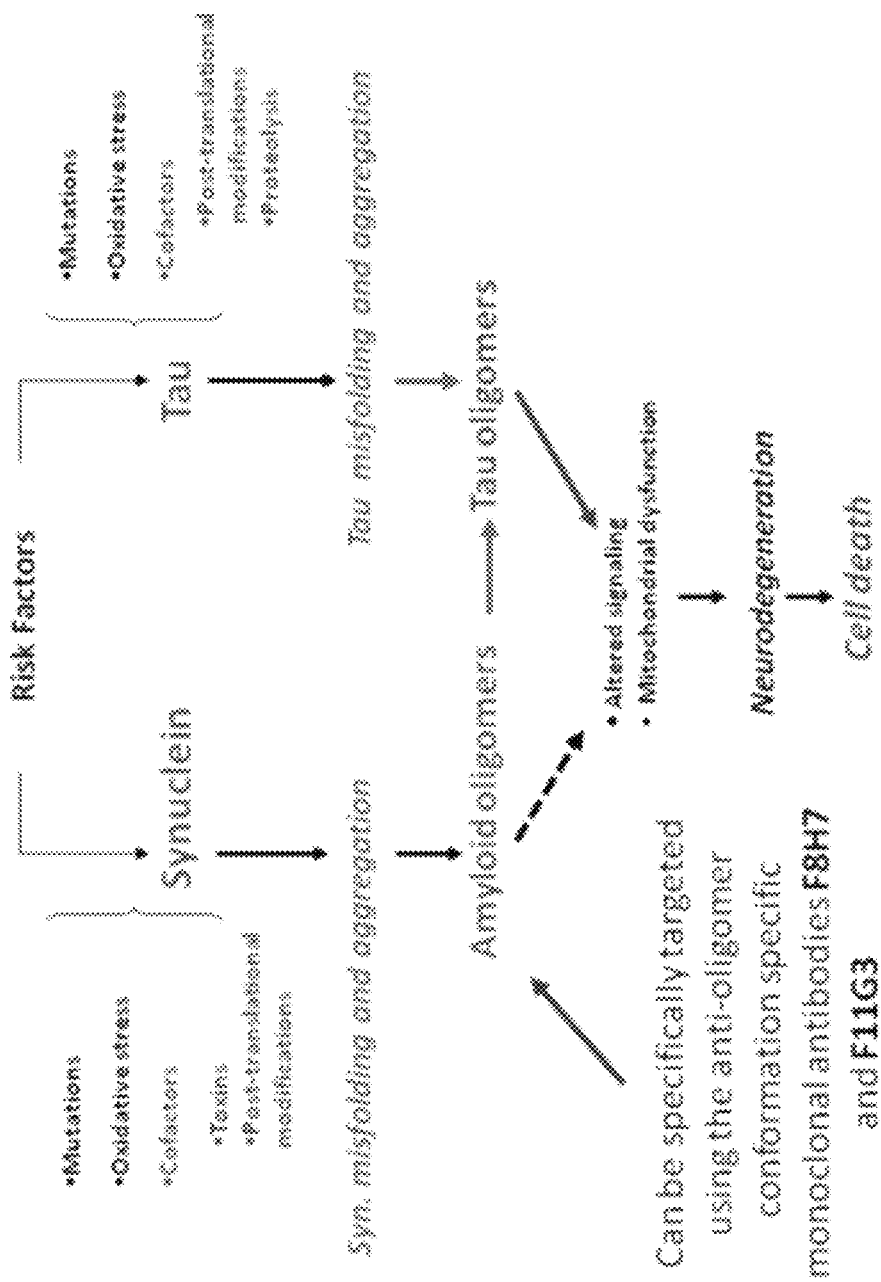

Anti-oligomer antibodies or AG712 oligomers can be administered to P301 L amyloid (JNPL3) model of amyloid related disease. JNPL3 mice have been used effectively in an active vaccination study directed at targeting amyloid aggregates. Tg2576 mice can be administered anti-oligomer antibodies or AG712 oligomers for the study of therapeutic effects of a polypeptide composition. Mice are vaccinated at various ages, and comprehensive behavioral assessments are performed before and after vaccination, including, fear conditioning, object recognition, locomotor activity, rotarod, and traverse beam. Anti-oligomer antibodies of the invention have also been shown to prevent oligomer toxicity (FIG. 8).

Correlation of Amyloid Oligomers with Pathology in AD Brain and CSF.

The presence, distribution and posttranslational modifications of amyloid oligomers can be measured and analyzed in post mortem brain and CSF samples. Immunohistochemical and biochemical analyses are performed using anti-oligomer antibodies and other available antibodies.

Immunohistochemical Analysis of Amyloid Oligomers in AD Brain.

Immunohistochemistry of the brain details the multiple types of aggregates present in AD brain. NFT in AD brain have been studied extensively. IHC analysis of brain samples is done using anti-oligomer antibodies in combination with antibodies that bind amyloid 5, HT7, pThr231, p422, AT100, AT8 and pSer396.

Patient and Brain Tissue Selection:

Frozen brain tissues can be assessed for amyloid pathology. Tissues are examined from transentorhinal cortex and cerebellum, entorhinal cortex, and hippocampus (Brodmann's Area's 11, 9 and 4).

Typically the sample information should have the clinical and pathological details of the patient such as patient age, gender and post-mortem index (PMI); mini mental state examination (MMSE) score; clinical dementia rating (CDR) score; and cognitive ability screening instrument (CASI) score.

Antibody Selection:

Samples are analyzed using the novel anti-oligomer monoclonal antibodies and other control antibodies (Kayed et al., 2003; Meier et al., 2006; Kayed et al., 2007; Kayed et al., 2009).

Tissue Processing:

Brain samples are fixed in a 10% neutral buffered formalin solution under standard conditions for neuropathological purposes. Samples from each brain are processed for paraffin embedding according to conventional methods and for frozen sections. The reason to work with both type of tissue preparation is that some antibodies work better in paraffin embedded sections than in frozen sections or vice versa. Furthermore, some antibodies react better with the DAB detection method, but not with fluorescent secondary antibodies or vice versa. The reactivity of anti-oligomer antibodies on post mortem human brain tissue is evaluated empirically using varying antibody dilution and carefully control staining Data Analysis:

Bright-field Images are typically acquire using a Nikon Eclipse 800 microscope equipped with a Nikon DXM1200 color CCD camera controlled by ACT-1 acquisition software (Nikon Instruments Inc., Melville, N.Y.). The fluorescent images are examined using a confocal microscope Zeiss LSM 510 (Zeiss, Hornwood, N.Y.) equipped with three laser lines. Argon ion laser with 4 lines of excitation: 458, 477, 488, 514 nm, Green He/Ne with excitation at 543 nm and Red He/Ne with excitation at 633 nm. To quantify the immunoreactivity, brain samples are analyzed using Stereo Investigator (MBF Bioscience, Williston, Vt.). A region of interest is outlined and the area fraction fractionator probe is used systematically and randomly, allocated sampling sites 400 µm apart. At each sampling site, 100×80 µm counting frame is superposed, containing markers equally spaced from one another at a distance of 15 µm. The markers that co-localize with anti-oligomer antibody immunoreactivity are labeled as positive, whereas remaining markers are labeled negative. The area fraction is calculated as the number of positive markers divided by the total number of markers. The stereological assessment is made in a blinded fashion. The statistical analysis for the area fraction of anti-oligomer antibody immunoreactivity is performed using one-way ANOVA followed by Bonferroni's multiple comparison test to allow for comparisons between groups. All statistical analysis is performed using GraphPAd Prism version 5.00 for Windows, (GraphPAd Software, San Diego, Calif.).

Western Blot and Dot Blot Analysis of Human Brain Tissue.

To determine if the progression of disease can be observed with anti-oligomer antibodies, a large population of brains from patients with a broad range with respect to Mini Mental Status and Braak & Braak changes are analyzed. Frozen tissue from AD, MCI and age matched controls are tested. The regions of interest examined include entorhinal cortex, hippocampus, parietal lobe, olfactory bulb and frontal cortex. The PBS fraction, Triton X-100 fraction, and the Triton insoluble fraction are analyzed by western blot.

Quantification of Amyloid Oligomers in CSF Samples by Direct ELISA:

A standard ELISA protocol is used: 20-50 µl of CSF (16-40 µg total protein) is used in triplicate for each experiment and is measured in at least two independent experiments, anti-oligomer antibody are used.

Quantification of Amyloid Oligomers in CSF Samples by IP/Western:

Standard protocols are used, both anti-oligomer antibody are used to coat beads. For IP, 0.5-1 ml CSF is used in each experiment. The samples are probed on western using anti-oligomer antibody.

Passive Vaccination Using Anti-Oligomer Antibodies.

The P301L model develops minor sensorimotor abnormalities by 3 months and NFT at 4 months old. Groups of mice ages 3, 4, 6, 7, and 9 months are vaccinated by a single bolus i.c.v injection of 2 µg of anti-oligomer antibody in the left hemisphere; control mice are i.c.v. injected with PBS or control IgG. Behavioral analyses are performed 3 days prior to the injection and 4 days after the injection. These tests include Rotarod, and Traverse beam and Object recognition. Animals are terminated 1 week after the injection; brains are extracted and dissected for ICH and biochemical analyses. A longer time between injection and the termination of the animal is also contemplated; this will help in understanding the dynamics between amyloid oligomers and other amyloid aggregates. The IHC analyses from these brains are used to evaluate the relationship between extracellular and intracellular amyloid oligomers.

Passive Vaccination of the AD Model Tg2576 Using Anti-Oligomer Antibody.

The Tg2576 model shows memory decline starting at 6 months, whereas Aβ amyloid plaques start to deposit at 9 months. These animals show severe memory deficits between 6-12 months old; Aβ oligomers at 6 months, long before plaque formation, groups of mice ages 6, 8, 10, and 12 months are vaccinated by i.c.v injection of 2 μg anti-oligomer antibody in the left hemisphere; control mice are i.c.v. injected with PBS or control IgG. Behavioral and memory tests are performed 4 days prior to the injection and 4 days after the injection; these tests include fear-conditioning and locomotor activity. Animals are terminated 1 week after the injection; brains are extracted and dissected for IHC and biochemical analysis.

The invention claimed is:

1. A monoclonal antibody or antibody fragment that specifically binds an oligomer comprising a peptide having the amino acid sequence of SEQ ID NO:1.

2. The monoclonal antibody or antibody fragment of claim 1, wherein the monoclonal antibody or antibody fragment is a mouse monoclonal antibody or mouse antibody fragment.

3. The monoclonal antibody or antibody fragment of claim 1, wherein the antibody is a single chain antibody.

4. The monoclonal antibody or antibody fragment of claim 1, wherein the monoclonal antibody or antibody fragment is a humanized monoclonal antibody or antibody fragment.

5. The monoclonal antibody or antibody fragment of claim 1, wherein the monoclonal antibody or antibody fragment comprises the amino acid sequence of SEQ ID NO:11 and SEQ ID NO:12.

6. A composition comprising an antibody of claim 1.

7. The composition of claim 6, wherein the composition is a pharmaceutically acceptable formulation.

* * * * *

SEQUENCE LISTING

```
<160> NUMBER OF SEQ ID NOS: 12

<210> SEQ ID NO 1
<211> LENGTH: 41
<212> TYPE: PRT
<213> ORGANISM: Artificial Sequence
<220> FEATURE:
<223> OTHER INFORMATION: synthetic peptide

<400> SEQUENCE: 1

Gly Lys His Gly Ala Gly Ala Ala Ala Ala Gly Ala Val Val Gly Gly
1               5                   10                  15

Leu Gly Gly Tyr Gly Leu Gly Ser Ala Gly Ser Arg Pro Ile Ile His
            20                  25                  30

Phe Gly Ser Asp Tyr Glu Asp Arg Tyr
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 37
<212> TYPE: PRT
<213> ORGANISM: Homo sapiens

<400> SEQUENCE: 4

Lys Cys Asn Thr Ala Thr Cys Ala Thr Gln Arg Leu Ala Asn Phe Leu
1               5                   10                  15
```

```
Val His Ser Ser Asn Asn Phe Gly Ala Ile Leu Ser Ser Thr Asn Val
            20                  25                  30

Gly Ser Asn Thr Tyr
            35

<210> SEQ ID NO 5
<211> LENGTH: 21
<212> TYPE: PRT
<213> ORGANISM: Homo sapiens

<400> SEQUENCE: 5

Lys Thr Asn Met Lys His Met Ala Gly Ala Ala Ala Ala Gly Ala Val
1               5                   10                  15

Val Gly Gly Leu Gly
            20

<210> SEQ ID NO 6
<211> LENGTH: 44
<212> TYPE: PRT
<213> ORGANISM: Artificial Sequence
<220> FEATURE:
<223> OTHER INFORMATION: Synthetic peptide

<400> SEQUENCE: 6

Lys Lys Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln Gln Gln Gln Gln Lys Lys
            35                  40

<210> SEQ ID NO 7
<211> LENGTH: 147
<212> TYPE: PRT
<213> ORGANISM: Homo sapiens

<400> SEQUENCE: 7

Met Lys Ala Leu Ile Val Leu Gly Leu Val Leu Leu Ser Val Thr Val
1               5                   10                  15

Gln Gly Lys Val Phe Glu Arg Cys Glu Leu Ala Arg Thr Leu Lys Arg
            20                  25                  30

Leu Gly Met Asp Gly Tyr Arg Gly Ser Leu Ala Asn Trp Met Cys Leu
            35                  40                  45

Ala Lys Trp Glu Ser Gly Tyr Asn Thr Arg Ala Thr Asn Tyr Asn Ala
        50                  55                  60

Gly Asp Arg Ser Thr Asp Tyr Gly Ile Phe Gln Ile Asn Ser Arg Tyr
65                  70                  75                  80

Trp Cys Asn Asp Gly Lys Thr Pro Gly Ala Val Asn Ala Cys His Leu
                85                  90                  95

Ser Cys Ser Ala Leu Leu Gln Asp Asn Ile Ala Asp Ala Val Ala Cys
            100                 105                 110

Ala Lys Arg Val Val Arg Asp Pro Gln Gly Ile Arg Ala Trp Val Ala
        115                 120                 125

Trp Arg Asn Arg Cys Gln Asn Arg Asp Val Arg Gln Tyr Val Gln Gly
    130                 135                 140

Cys Gly Val
145
```

```
<210> SEQ ID NO 8
<211> LENGTH: 110
<212> TYPE: PRT
<213> ORGANISM: Homo sapiens

<400> SEQUENCE: 8
```

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

```
<210> SEQ ID NO 9
<211> LENGTH: 147
<212> TYPE: PRT
<213> ORGANISM: Homo sapiens

<400> SEQUENCE: 9
```

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

```
<210> SEQ ID NO 10
<211> LENGTH: 140
<212> TYPE: PRT
<213> ORGANISM: Homo sapiens

<400> SEQUENCE: 10
```

Met Asp Val Phe Met Lys Gly Leu Ser Lys Ala Lys Glu Gly Val Val
1               5                   10                  15

```
Ala Ala Ala Glu Lys Thr Lys Gln Gly Val Ala Glu Ala Ala Gly Lys
             20                  25                  30

Thr Lys Glu Gly Val Leu Tyr Val Gly Ser Lys Thr Lys Glu Gly Val
         35                  40                  45

Val His Gly Val Ala Thr Val Ala Glu Lys Thr Lys Glu Gln Val Thr
     50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
             85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

<210> SEQ ID NO 11
<211> LENGTH: 120
<212> TYPE: PRT
<213> ORGANISM: Mus musculus

<400> SEQUENCE: 11

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Asp Tyr
             20                  25                  30

Tyr Met Lys Trp Val Lys Gln Ser His Gly Lys Ser Leu Glu Trp Ile
         35                  40                  45

Gly Asp Ile Asn Pro Asn Asn Gly Asp Thr Phe Tyr Asn Gln Lys Phe
     50                  55                  60

Lys Gly Lys Ala Thr Leu Thr Val Asp Lys Ser Ser Thr Ala Tyr
 65                  70                  75                  80

Met Gln Leu Asn Ser Leu Thr Ser Glu Asp Ser Ala Val Tyr Tyr Cys
             85                  90                  95

Ala Arg Gly Val Tyr Asp Gly Tyr Tyr Ala Met Asp Tyr Trp Gly Gln
            100                 105                 110

Gly Thr Ser Val Thr Val Ser Ser
            115                 120

<210> SEQ ID NO 12
<211> LENGTH: 112
<212> TYPE: PRT
<213> ORGANISM: Mus musculus

<400> SEQUENCE: 12

Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
             20                  25                  30
```

```
Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110
```